US00PP16337P3

(12) United States Plant Patent
Kaagman

(10) Patent No.: US PP16,337 P3
(45) Date of Patent: Mar. 14, 2006

(54) *OSTEOSPERMUM* PLANT NAMED 'OSTE LIGHTPUR'

(50) Latin Name: *Osteospermum ecklonis*
Varietal Denomination: Oste Lightpur

(75) Inventor: Pim Kaagman, Andijk (NL)

(73) Assignee: Glodsmith Seeds, Inc., Gilroy, CA (US)

( * ) Notice: Subject to any disclaimer, the term of this patent is extended or adjusted under 35 U.S.C. 154(b) by 145 days.

(21) Appl. No.: 10/885,565

(22) Filed: Jul. 6, 2004

(65) Prior Publication Data

US 2006/0010547 P1 Jan. 12, 2006

(51) Int. Cl.
*A01H 5/00* (2006.01)

(52) U.S. Cl. ..... Plt./360

(58) Field of Classification Search ..... Plt./360
See application file for complete search history.

(56) References Cited

PUBLICATIONS

The New Royal Horticultural Society Dictionary of Gardening, 1992. 1, A to C, pp. xxxv and xlii.*

* cited by examiner

*Primary Examiner*—Anne Marie Grunberg
*Assistant Examiner*—June Hwu
(74) *Attorney, Agent, or Firm*—Jondle & Associates, P.C.

(57) ABSTRACT

An *Osteospermum* cultivar particularly distinguished by violet colored flowers, dark green foliage and vigorous growth is described.

1 Drawing Sheet

Genus and species: *Osteospermum ecklonis.*
Variety denomination: 'Oste Lightpur'.

BACKGROUND OF THE NEW PLANT

The variety 'Oste Lightpur' originated from a cross made in October, 2000. The female parent is a violet proprietary line OX-49 (unpatented). The male parent is 'Denebola', (patent status unknown) which is a violet commercial variety. Seed from this cross was sown in June 2001. In October 2001, single-plant selections were made for vegetative propagation using plant habit and flower color as selection criteria. One selection became the new variety 'Oste Lightpur'.

'Oste Lightpur' is a product of a planned breeding program intended to create new *Osteospermum* cultivars with violet colored flowers, dark green foliage, and vigorous growth.

The new cultivar was created in 2000 in Gilroy, Calif. and has been asexually reproduced repeatedly by vegetative cuttings and tissue culture in Gilroy, Calif.; and Andijk, The Netherlands over a two ½ year period. The plant has also been trialed at Gilroy, Calif.; and Andijk, The Netherlands. The present invention has been found to retain its distinctive characteristics through successive propagation, and this novelty is firmly fixed.

DESCRIPTION OF PHOTOGRAPH

This new *Osteospermum* plant is illustrated by the accompanying photograph which shows blooms, buds, and foliage of the plant in full color, the colors shown being as true as can be reasonably obtained by conventional photographic procedures. Photos were taken from plants grown in The Netherlands in the late winter/spring in a greenhouse. Plants are 4½ months old, had one terminal pinch at 3 weeks old, and are grown in a 4 inch pot with 3 treatments of cyocel.

The photograph shows the mature plant with an inset photo of a close-up of the inflorescence.

DESCRIPTION OF THE NEW CULTIVAR

The following detailed descriptions set forth the distinctive characteristics of 'Oste Lightpur'. The data, which defines these characteristics, were collected from asexual reproductions carried out in Gilroy, Calif. The plant history was taken on 6 month old plants grown in one gallon pots in the late winter/spring season, in a LEXAN covered greenhouse under natural light and color readings were taken in the greenhouse under natural lights. Color references are primarily to The R.H.S. Colour Chart of The Royal Horticultural Society of London (R.H.S.) 2001. Texture description details were observed under a dissecting microscope according to The New Royal Horticultural Society Dictionary of Gardening (1992).

THE PLANT

Classification: *Osteospermum ecklonis.*
Botanical: *Osteospermum.*
Commercial: 'Oste Lightpur'.
Form: Upright, semi-compact and mounded.
Growth and branching habit: Good vigorous, freely branched habit.
Height: From soil level to top of blooms: Approximately 37–43 cm.
Width: Approximately 25–35 cm.
Time to produce a finished flowering plant: 8–11 weeks for a 6 inch pot.
Outdoor plant performance: Herbaceous, frost tender perennial patio planters, mixed container plantings or garden beds.
Time to initiate and develop roots: Approximately 8–14 days in the greenhouse.
Root description: Fibrous, well-branched, white.

THE LEAVES

Leaf arrangement: Alternate.
Fully expanded, Length: 5.3–5.5 cm; Width: 3.1–3.5 cm.
Leaf shape: Obovate.
Leaf margin: Dentate.
Apex aspect: Broadly acute.
Base aspect: Acuminate.
Leaf color: Upper surface — RHS 137A (green) but a little darker; Under surface RHS 137B (green).
Leaf texture: Pilose.
Venation: Pinnate.
Venation color: RHS 144C (yellow-green) but a little lighter.
Petiole length: 0.5–0.7 cm.
Petiole diameter: 0.3 cm.
Petiole color: RHS 144C (yellow-green).
Petiole texture: Pilose.

THE STEM

Length: 30–40 cm.
Diameter: 0.3 cm.
Stem internode length: 1.5–2.5 cm.
Color: RHS 144B (yellow-green).
Texture: Pilose.
Stem anthocyanin: None.
Peduncle color: RHS 144A (yellow-green).
Peduncle length: 7.5–14.0 cm.
Peduncle diameter: 0.2 cm.
Peduncle texture: Pilose.
Peduncle strength: Moderate to strong.

THE BUD

Shape: Ovate.
Diameter: 0.8–0.9 cm.
Length: 1.3–1.7 cm.
Color at tight bud (starting to show color): RHS N77B (purple).

THE FLOWER

Blooming habit: Plants flower freely from the spring through fall given the proper growing conditions.
Inflorescence/floret type: Terminal and axillary inflorescences held above the foliage. Capitulum inflorescence, radially symmetrical.
Flower diameter: 5.5–6.0 cm.
Average disc diameter: 1.0 cm.
Ray floret, immature and mature color: Upper surface is a shading mixture of RHS N74C (red-purple) and 75A (purple). Under surface is RHS N77C (purple) with longitudinal stripes of faded RHS N77A (purple).
*Floret length.*—2.7–3.0 cm.
*Floret width.*—0.7–0.8 cm.
*Floret apex shape.*—Emarginate to Retuse.
*Floret base shape.*—Cuneate.
*Floret margin.*—Entire.
*Floret texture.*—Papillose and hirsute on the basal margins.
*Floret quantity.*—Approximately 20.
Disc floret, tube color: RHS N155B (white) but whiter.
*Shape.*—Tubular, elongated.
*Length.*—0.6–0.7 cm.
*Diameter at apex.*—0.2 cm.
*Apex shape.*—5-pointed, acute.
*Apex color.*—RHS N79A (purple).
*Floret quantity.*—Approximately 75.
Phyllaries, color: RHS 138A (green).
*Length.*—1.0–1.2 cm.
*Width.*—0.15–0.2 cm.
*Shape.*—Linear.
*Apex.*—Acute.
*Texture.*—Pilose and glandular hairs.
*Longevity of individual blooms.*—7–14 days.
*Fragrance.*—None.

THE REPRODUCTIVE ORGANS

Androecium, pollen color: RHS 13A (yellow).
*Filament color.*—RHS N77C (purple).
*Length of stamen.*—0.3–0.5 cm.
*Location of androecium.*—Disc floret only.
Gynoecium, Pistil: 1 per floret.
*Pistil length.*—0.4 cm.
*Stigma color.*—RHS N79A (purple).
*Style color.*—RHS N155D (white) but whiter.
*Location of gynoecium.*—Both disc and ray florets.
*Fruit seed set.*—Has not been observed.

DISEASE AND INSECT RESISTANCE

Has not been observed.

COMPARISON WITH KNOWN CULTIVARS

'Oste Lightpur' differs from the female parent, OX-49 in the following ways: 'Oste Lightpur' is later to flower, more vigorous and a lighter flower color than OX-49.

'Oste Lightpur' differs from the male parent, 'Denebola' in the following ways: 'Oste Lightpur' is earlier to flower, has better branching and shorter flower stems than 'Denebola'.

'Oste Lightpur' differs from the commercial *Osteospermum* variety 'Sunny Martha' in the following ways: 'Oste Lightpur' is more compact and earlier to flower than 'Sunny Martha.' In addition, 'Oste Lightpur' has smaller leaves, lighter foliage, more branches and more flowers than 'Sunny Martha.'

I claim:

1. A new and distinct cultivar of *Osteospermum* plant as shown and described herein.

* * * * *

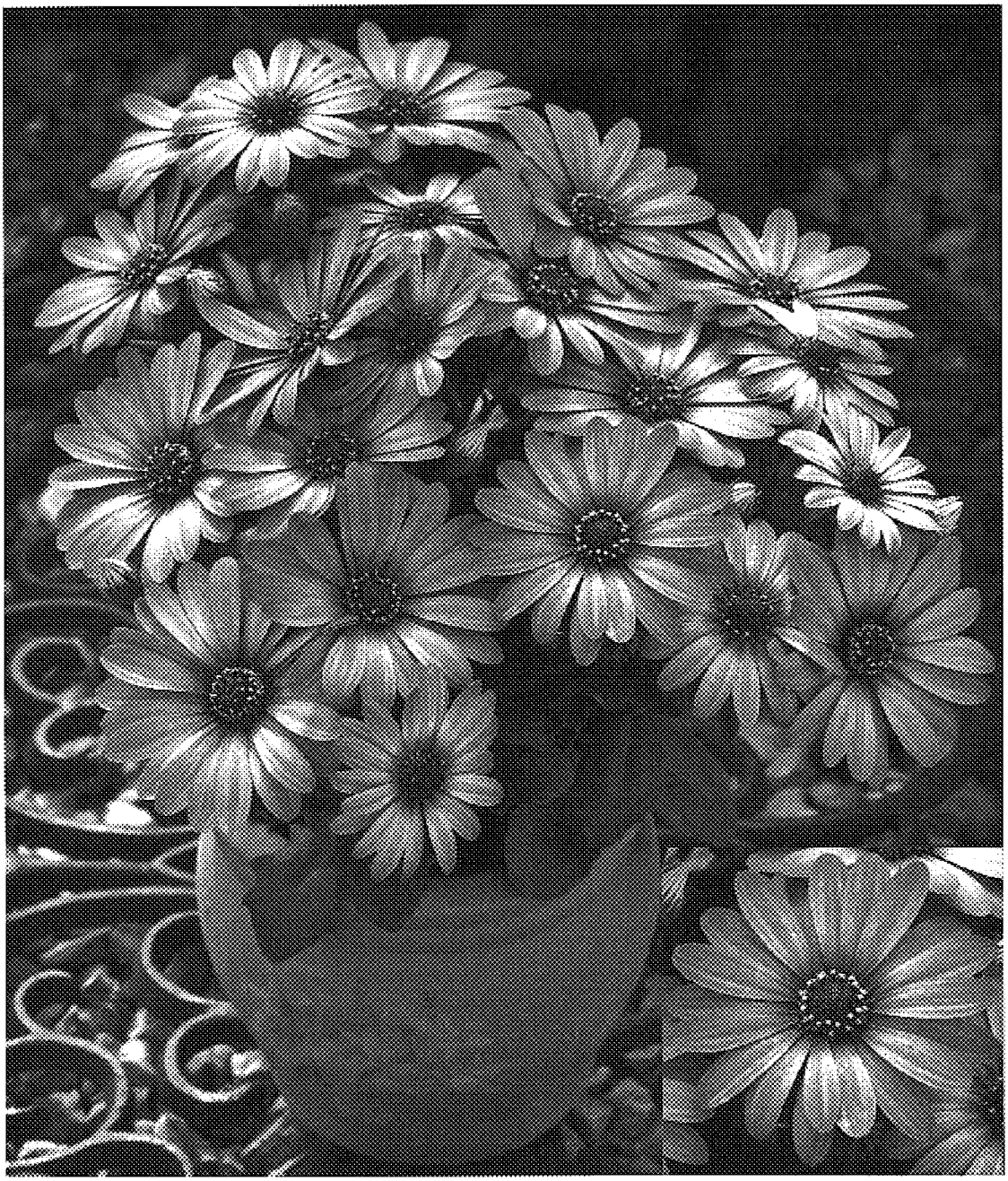

UNITED STATES PATENT AND TRADEMARK OFFICE

CERTIFICATE OF CORRECTION

PATENT NO. : PP 16,337 P3
APPLICATION NO. : 10/885565
DATED : March 14, 2006
INVENTOR(S) : Pim Kaagman It is certified that error appears in the above-identified patent and that said Letters Patent is hereby corrected as shown below:

Title Osteopermum Plant Named "'Oste "Lightpur'" should read Osteospermum Plant Named --'Oste Litpur'--

Varietal Denomination: "Oste Lightpur" should read --Oste Litpur--

Assignee: "Glodsmith" should read --Goldsmith--

Column 1, line 2, Variety denomination: "'Oste Lightpur'" should read --'Oste Litpur'--
Column 1, line 6, "'Oste Lightpur'" should read --'Oste Litpur'--
Column 1, line 13-14, "'Oste Lightpur'" should read --'Oste Litpur'--
Column 1, line 15, "'Oste Lightpur'" should read --'Oste Litpur'--

Column 2, line 7, "'Oste Lightpur'" should read --'Oste Litpur'--
Column 2, line 23, "'Oste Lightpur'" should read --'Oste Litpur'--

Column 4, line 40, "'Oste Lightpur'" should read --'Oste Litpur'--
Column 4, line 41, "'Oste Lightpur'" should read --'Oste Litpur'--
Column 4, line 43, "'Oste Lightpur'" should read --'Oste Litpur'--
Column 4, line 44, "'Oste Lightpur'" should read --'Oste Litpur'--
Column 4, line 47, "'Oste Lightpur'" should read --'Oste Litpur'--
Column 4, line 48-49, "'Oste Lightpur'" should read --'Oste Litpur'--
Column 4, line 50, "'Oste Lightpur'" should read --'Oste Litpur'--

Signed and Sealed this

Eighth Day of August, 2006

JON W. DUDAS
*Director of the United States Patent and Trademark Office*